(12) United States Patent
Lu

(10) Patent No.: US 10,768,315 B2
(45) Date of Patent: Sep. 8, 2020

(54) POSITRON EMISSION TOMOGRAPHY DETECTING DEVICE

(71) Applicant: SHANGHAI UNITED IMAGING HEALTHCARE CO., LTD., Shanghai (CN)

(72) Inventor: Ting Lu, Shanghai (CN)

(73) Assignee: SHANGHAI UNITED IMAGING HEALTHCARE CO., LTD., Shanghai (CN)

( * ) Notice: Subject to any disclaimer, the term of this patent is extended or adjusted under 35 U.S.C. 154(b) by 0 days.

(21) Appl. No.: 15/826,756

(22) Filed: Nov. 30, 2017

(65) Prior Publication Data

US 2019/0033471 A1 Jan. 31, 2019

Related U.S. Application Data

(63) Continuation of application No. PCT/CN2017/095069, filed on Jul. 28, 2017.

(51) Int. Cl.
*G01T 1/20* (2006.01)
*G01T 1/29* (2006.01)
(Continued)

(52) U.S. Cl.
CPC .......... *G01T 1/2018* (2013.01); *G01T 1/2985* (2013.01); *G01T 1/00* (2013.01);
(Continued)

(58) Field of Classification Search
CPC ........ G01T 1/2018; G01T 1/208; G01T 1/20; G01T 1/248; G01T 1/00; G01T 1/1612; G01T 1/1617; G01T 1/17; G01T 1/247
(Continued)

(56) References Cited

U.S. PATENT DOCUMENTS 3,594,577 A 7/1971 Loveday
6,297,506 B1 10/2001 Young et al.
(Continued)

FOREIGN PATENT DOCUMENTS

CN 104252005 A 12/2014
CN 104793231 A 7/2015
(Continued)

OTHER PUBLICATIONS

International Search Report in PCT/CN2017/095069 dated Apr. 25, 2018, 5 pages.
(Continued)

*Primary Examiner* — Taeho Jo
(74) *Attorney, Agent, or Firm* — Metis IP LLC

(57) ABSTRACT

A PET detecting device may include a plurality of detection modules and a processing engine. Each of the plurality of detection modules may include a scintillator array, one or more photoelectric converters, one or more energy information determination circuits and a time information determination circuit. The scintillator array may interact with a plurality of photons at respective interaction points to generate a plurality of optical signals. The one or more photoelectric converters may convert the plurality of optical signals to one or more electric signals that each include an energy signal and a time signal. The one or more energy information determination circuits may generate energy information based on the one or more energy signals. The time information determination circuit may generate time information based on the one or more time signals. The processing engine may generate an image based on the energy information and the time information.

19 Claims, 8 Drawing Sheets

(51) Int. Cl.
    *G01T 1/208* (2006.01)
    *G01T 1/00* (2006.01)
    *G01T 1/161* (2006.01)
    *G01T 1/24* (2006.01)
    *G01T 1/17* (2006.01)

(52) U.S. Cl.
    CPC .............. *G01T 1/1612* (2013.01); *G01T 1/17* (2013.01); *G01T 1/20* (2013.01); *G01T 1/208* (2013.01); *G01T 1/247* (2013.01); *G01T 1/248* (2013.01)

(58) Field of Classification Search
    USPC ..................................................... 250/363.03
    See application file for complete search history.

(56) References Cited

U.S. PATENT DOCUMENTS

| | | | |
|---|---|---|---|
| 7,403,589 B1 | 7/2008 | Short et al. | |
| 8,258,480 B2* | 9/2012 | Olcott | G01T 1/1647 |
| | | | 250/363.02 |
| 8,384,037 B2 | 2/2013 | Aykac et al. | |
| 8,880,144 B2* | 11/2014 | Kang | G01T 1/2935 |
| | | | 250/363.03 |
| 9,006,664 B2* | 4/2015 | Zhang | G01T 1/2018 |
| | | | 250/363.01 |
| 2003/0141906 A1* | 7/2003 | Tumer | H04N 5/335 |
| | | | 327/69 |
| 2004/0021082 A1* | 2/2004 | Wong | G01T 1/208 |
| | | | 250/367 |
| 2004/0200966 A1* | 10/2004 | Ramsden | G01T 1/2985 |
| | | | 250/367 |
| 2004/0239377 A1* | 12/2004 | Tumer | G01T 1/17 |
| | | | 327/94 |
| 2008/0099689 A1* | 5/2008 | Nygard | G01T 1/2018 |
| | | | 250/370.09 |
| 2009/0236532 A1* | 9/2009 | Frach | G01T 1/1611 |
| | | | 250/363.04 |
| 2010/0025589 A1* | 2/2010 | Olcott | G01T 1/1647 |
| | | | 250/363.03 |
| 2010/0084560 A1 | 4/2010 | Aykac et al. | |
| 2010/0150311 A1* | 6/2010 | Takasawa | G16H 40/60 |
| | | | 378/98 |
| 2011/0017918 A1 | 1/2011 | Baeumer et al. | |
| 2011/0127435 A1* | 6/2011 | Nakamura | G01T 1/1644 |
| | | | 250/362 |
| 2011/0210255 A1* | 9/2011 | Kim | G01T 1/2985 |
| | | | 250/362 |
| 2011/0263965 A1* | 10/2011 | Kang | G01T 1/2985 |
| | | | 600/411 |
| 2011/0297835 A1* | 12/2011 | Yamada | G01T 1/1612 |
| | | | 250/363.03 |
| 2012/0056097 A1* | 3/2012 | Takasawa | G01J 1/42 |
| | | | 250/394 |
| 2012/0212355 A1* | 8/2012 | Zhang | G01T 1/2018 |
| | | | 341/50 |
| 2013/0264484 A1* | 10/2013 | Myung | G01T 1/164 |
| | | | 250/363.03 |
| 2013/0320218 A1* | 12/2013 | Woldemichael | G01T 1/2985 |
| | | | 250/362 |
| 2014/0021356 A1* | 1/2014 | Zwaans | G01T 1/2985 |
| | | | 250/362 |
| 2015/0028218 A1* | 1/2015 | Kataoka | G01T 1/1642 |
| | | | 250/367 |
| 2015/0069250 A1* | 3/2015 | Schmand | G01T 1/208 |
| | | | 250/362 |
| 2015/0168567 A1* | 6/2015 | Kim | G01T 1/248 |
| | | | 250/370.11 |
| 2015/0309192 A1* | 10/2015 | Coelho Dos Santos Varela | ......... |
| | | | G01T 1/2985 |
| | | | 250/370.06 |
| 2016/0054455 A1* | 2/2016 | Teshigawara | A61B 6/4258 |
| | | | 600/411 |
| 2016/0084703 A1* | 3/2016 | Shaber | G01J 1/44 |
| | | | 250/336.1 |
| 2016/0170045 A1* | 6/2016 | Kim | G01T 1/2985 |
| | | | 250/208.1 |
| 2016/0299002 A1* | 10/2016 | Steadman Booker | G01J 1/44 |
| 2017/0123078 A1* | 5/2017 | Ota | G01T 1/2985 |
| 2017/0234990 A1* | 8/2017 | Sowards-Emmerd | ..................... |
| | | | G01T 1/2018 |
| | | | 250/362 |
| 2017/0276807 A1* | 9/2017 | Nishihara | H04N 5/378 |
| 2018/0059267 A1* | 3/2018 | Ng | G01T 1/161 |
| 2018/0284294 A1* | 10/2018 | Xie | G01T 1/1642 |
| 2019/0064369 A1* | 2/2019 | Chen | G01N 21/6408 |

FOREIGN PATENT DOCUMENTS

| | | |
|---|---|---|
| CN | 104932000 A | 9/2015 |
| CN | 205826876 U | 12/2016 |
| CN | 106443757 A | 2/2017 |

OTHER PUBLICATIONS

Written Opinion in PCT/CN2017/095069 dated Apr. 25, 2018, 5 pages.

* cited by examiner

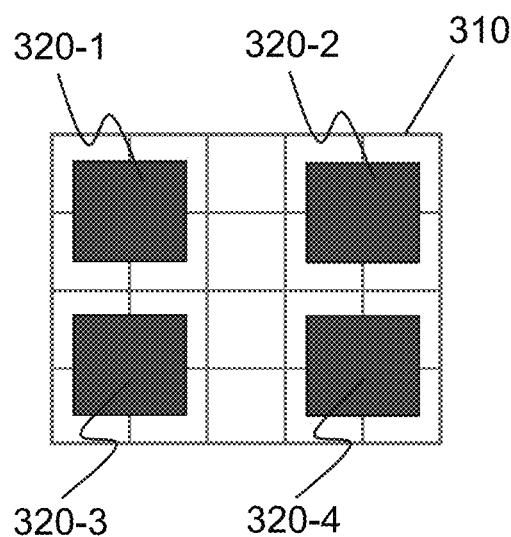
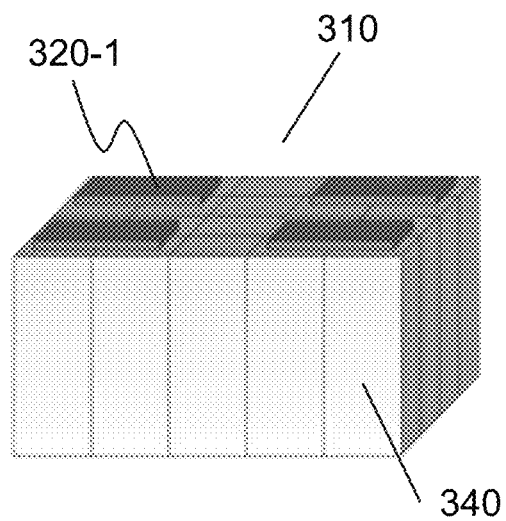
FIG. 3A    FIG. 3B
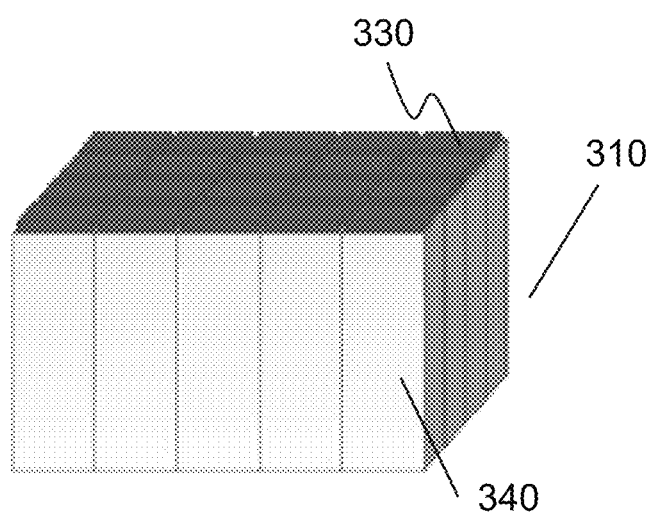
FIG. 3C

US 10,768,315 B2

POSITRON EMISSION TOMOGRAPHY DETECTING DEVICE

CROSS-REFERENCE TO RELATED APPLICATIONS

This present application is a continuation of International Application No. PCT/CN2017/095069, filed on Jul. 28, 2017, the contents of which are hereby incorporated by reference.

TECHNICAL FIELD

The present disclosure generally relates to positron emission tomography (PET), and more specifically, relates to a PET detecting device.

BACKGROUND

PET is a functional imaging technique in nuclear medicine that produces a three-dimensional image of functional processes in a living object. Typically, a short-lived radioactive isotope tracer, such as fluorodeoxyglucose (FDG), may be injected into the object. The tracer may undergo a positron emission decay (also known as beta decay) and emit a positron. The positron may annihilate with an electron and a pair of annihilation photons (or gamma photons) that move in approximately opposite directions.

A PET system may include a PET detection module configured to detect the photons. Typically, the detection module includes a scintillator array, one or more optical detecting components such as PhotoMultiplier Tubes (PMT) or Silicon Photomultipliers (SIPM), and a post-processing circuit. However, each of the PMT tubes may need an individual power supply and hence may make the detection module complex and unstable. SIPM may not require the individual power supply, but each of the SIPM may be connected to a scintillation crystal of the scintillator array and a post-processing circuit. Based on this arrangement, the number of SIPM and the post-processing circuit may have to be increased if the number of scintillation crystals increases. As a result, the size of the detection module is limited and the cost is high.

SUMMARY

According to an aspect of the present disclosure, a device is provided. The device may include a plurality of detection modules and a processing engine. Each of the plurality of detection modules may include a scintillator array, one or more photoelectric converters, one or more energy information determination circuits and a time information determination circuit. The scintillator array may interact with a plurality of photons at respective interaction points to generate a plurality of optical signals. The one or more photoelectric converters may be coupled to the scintillator array and may be configured to convert the plurality of optical signals to one or more electric signals. The one or more electric signals may each include an energy signal and a time signal. The one or more energy information determination circuits may be configured to generate energy information based on the one or more energy signals. The at least one energy information determination circuit may each connect to at least one photoelectric converter of the one or more photoelectric converters. The time information determination circuit may be connected to the one or more photoelectric converters and may be configured to generate time information based on the one or more time signals. The processing engine may be configured to generate an image based on the energy information and the time information.

In some embodiments, the scintillator array may include a plurality of scintillation crystals. Each of the one or more photoelectric converters may be coupled to one or more of the plurality of scintillation crystals.

In some embodiments, the one or more photoelectric converters may be arranged in M rows and N columns, and the one or more energy information determination circuit may include M first energy information determination circuits and N second energy information determination circuits. Each of the M first energy information determination circuits is connected to one of the M rows of photoelectric converters and each of the N second energy information determination circuits is connected to one of the N columns of photoelectric converters.

In some embodiments, the M and the N each is an integer from 1 to 20.

In some embodiments, the M and the N are equal to 2.

In some embodiments, each of the M first energy information determination circuits and the N second energy information determination circuits may include a differential adder and an analog to digital converter (ADC).

In some embodiments, the device may further include a decoder. The decoder may be connected to the at least one energy information determination circuit and may be configured to determine locations of the interaction points based on the energy information.

In some embodiments, the time information determination circuit may include a differential unit configured to process the one or more time signals to generate an accelerated time signal, a comparator configured to generate a trigger signal based on the accelerated time signal, and a time-to-digital converter (TDC) configured to generate the time information based on the trigger signal.

In some embodiments, the time information may include a time point when the scintillator array interacts with the plurality of photons.

In some embodiments, the scintillator array is made of bismuth germanium oxide (BGO) crystals, lutetium-yttrium oxyorthosilicate (LYSO) crystals, or lutetium oxyorthosilicate (LSO) crystals.

In some embodiments, the photoelectric converter is a photomultiplier (PTM), an avalanche photodiode (APD), or a silicon photomultiplier (SIPM).

According to another aspect of the present disclosure, a system is provided. The system may include a gantry, a detector and a processing engine. The gantry may include a detecting area in which an object is scanned. The detector may be configured to receive a plurality of photons that are emitted from the object. The detector may include a plurality of detection modules. Each of the plurality of detection modules may include a scintillator array, one or more photoelectric converters, one or more energy information determination circuits and a time information determination circuit. The scintillator array may interact with a plurality of photons at respective interaction points to generate a plurality of optical signals. The one or more photoelectric converters may be coupled to the scintillator array and may be configured to convert the plurality of optical signals to one or more electric signals. The one or more electric signals may each include an energy signal and a time signal. The one or more energy information determination circuits may be configured to generate energy information based on the one or more energy signals. The at least one energy information determination circuit may each connect to at least one photoelectric converter of the one or more photoelectric converters. The time information determination circuit may be connected to the one or more photoelectric converters and may be configured to generate time information based on the one or more time signals. The processing engine may be configured to generate an image based on the energy information and the time information.

According to another aspect of the present disclosure, a method is provided. The method may include interacting with a plurality of photons at respective interaction points to generate a plurality of optical signals and converting the plurality of optical signals to one or more electric signals. The one or more electric signals may each include an energy signal and a time signal. The method may further include generating energy information based on the one or more energy signals, generating time information based on the one or more time signals, and generating an image based on the energy information and the time information.

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities and combinations set forth in the detailed examples discussed below.

BRIEF DESCRIPTION OF THE DRAWINGS

The present disclosure is further described in terms of exemplary embodiments. These exemplary embodiments are described in detail with reference to the drawings. These embodiments are non-limiting exemplary embodiments, in which like reference numerals represent similar structures throughout the several views of the drawings, and wherein:

FIGS. 3A-3C are schematic diagrams illustrating an exemplary detection module according to some embodiments of the present disclosure;

DETAILED DESCRIPTION

In the following detailed description, numerous specific details are set forth by way of examples in order to provide a thorough understanding of the relevant disclosure. However, it should be apparent to those skilled in the art that the present disclosure may be practiced without such details. In other instances, well-known methods, procedures, systems, components, and/or circuitry have been described at a relatively high-level, without detail, in order to avoid unnecessarily obscuring aspects of the present disclosure. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown, but to be accorded the widest scope consistent with the claims.

The terminology used herein is for the purpose of describing particular example embodiments only and is not intended to be limiting. As used herein, the singular forms "a," "an," and "the" may be intended to include the plural forms as well, unless the context clearly indicates otherwise. It will be further understood that the terms "comprise," "comprises," and/or "comprising," "include," "includes," and/or "including," when used in this specification, specify the presence of stated features, integers, steps, operations, elements, and/or components, but do not preclude the presence or addition of one or more other features, integers, steps, operations, elements, components, and/or groups thereof.

It will be understood that the term "system," "engine," "unit," "module," and/or "block" used herein are one method to distinguish different components, elements, parts, section or assembly of different level in ascending order. However, the terms may be displaced by other expression if they achieve the same purpose.

Figure 1:
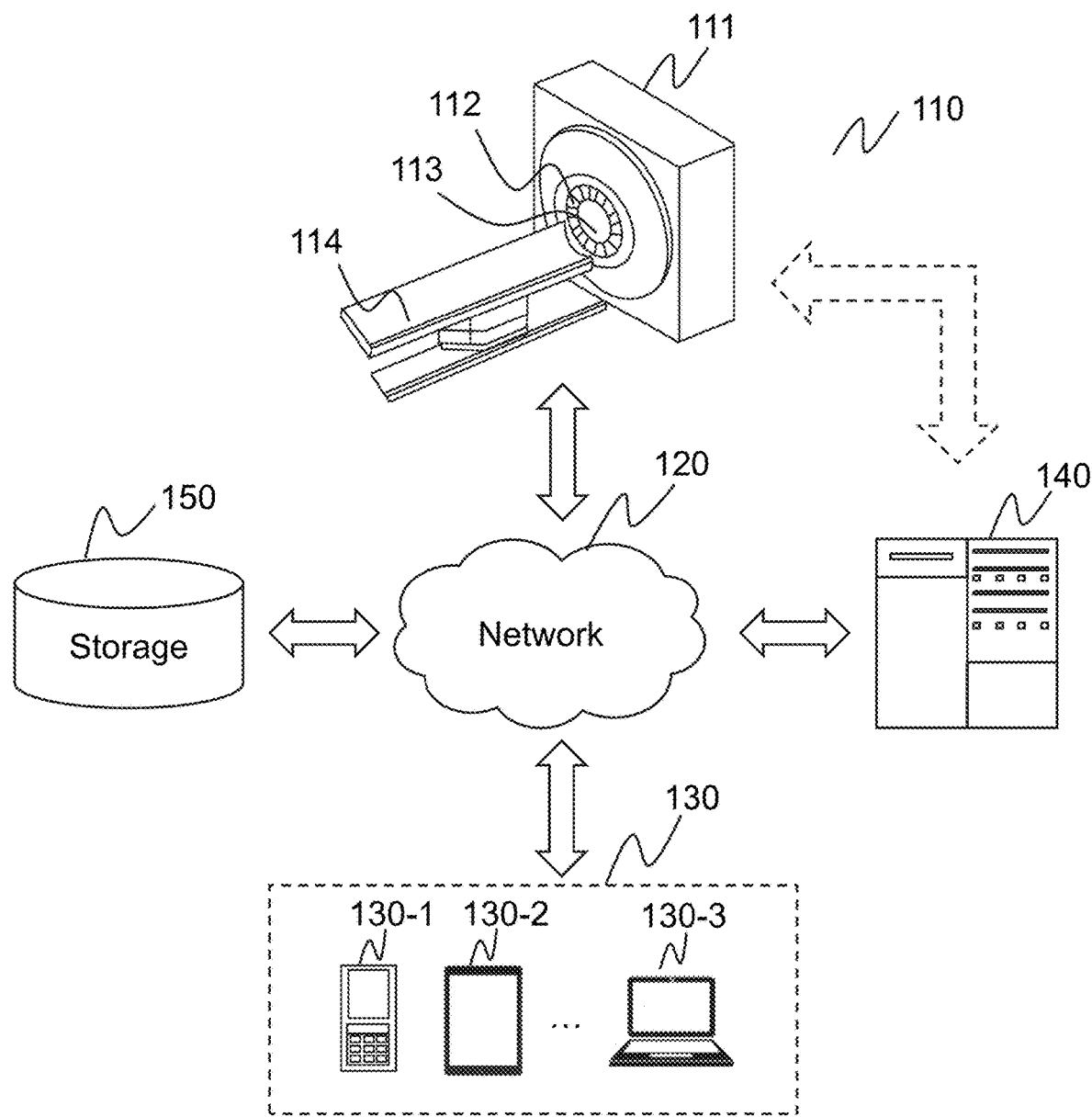
FIG. 1 is a schematic diagram illustrating an exemplary imaging system according to some embodiments of the present disclosure.

Generally, the word "module," "unit," or "block," as used herein, refers to logic embodied in hardware or firmware, or to a collection of software instructions. A module, a unit, or a block described herein may be implemented as software and/or hardware and may be stored in any type of non-transitory computer-readable medium or other storage device. In some embodiments, a software module/unit/block may be compiled and linked into an executable program. It will be appreciated that software modules can be callable from other modules/units/blocks or from themselves, and/or may be invoked in response to detected events or interrupts. Software modules/units/blocks configured for execution on computing devices (e.g., processing engine 140 as illustrated in FIG. 1) may be provided on a computer-readable medium, such as a compact disc, a digital video disc, a flash drive, a magnetic disc, or any other tangible medium, or as a digital download (and can be originally stored in a compressed or installable format that needs installation, decompression, or decryption prior to execution). Such software code may be stored, partially or fully, on a storage device of the executing computing device, for execution by the computing device. Software instructions may be embedded in a firmware, such as an EPROM. It will be further appreciated that hardware modules/units/blocks may be included in connected logic components, such as gates and flip-flops, and/or can be included of programmable units, such as programmable gate arrays or processors. The modules/units/blocks or computing device functionality described herein may be implemented as software modules/units/blocks, but may be represented in hardware or firmware. In general, the modules/units/blocks described herein refer to logical modules/units/blocks that may be combined with other modules/units/blocks or divided into sub-modules/sub-units/sub-blocks despite their physical organization or storage. The description may be applicable to a system, an engine, or a portion thereof.

It will be understood that when a unit, engine, module or block is referred to as being "on," "connected to," or "coupled to," another unit, engine, module, or block, it may be directly on, connected or coupled to, or communicate with the other unit, engine, module, or block, or an intervening unit, engine, module, or block may be present, unless the context clearly indicates otherwise. As used herein, the term "and/or" includes any and all combinations of one or more of the associated listed items.

These and other features, and characteristics of the present disclosure, as well as the methods of operation and functions of the related elements of structure and the combination of parts and economies of manufacture, may become more apparent upon consideration of the following description with reference to the accompanying drawings, all of which form a part of this disclosure. It is to be expressly understood, however, that the drawings are for the purpose of illustration and description only and are not intended to limit the scope of the present disclosure. It is understood that the drawings are not to scale.

FIG. 1 is a schematic diagram illustrating an exemplary imaging system 100 according to some embodiments of the present disclosure. In some embodiments, the imaging system 100 may be a single-modal system such as a positron emission tomography (PET) imaging system. Alternatively, the imaging system 100 may be a multi-modal system such as a positron emission tomography PET-CT imaging system, a PET-MRI imaging system, etc. As shown in FIG. 1, the imaging system 100 may include a scanner 110, a network 120, one or more terminals 130, a processing engine 140, and a storage 150. In some embodiments, the components in the imaging system 100 may be connected to each other via the network 120. Alternatively or additionally, the components in the imaging system 100 may be directly connected to each other.

The scanner 110 may scan an object and generate scanning data corresponding to the object. The object may include but is not limited to one or more organs, one or more tissues, or the like, of a patient. In some embodiments, the scanner 110 may be a medical scanning device, for example, a PET device, a PET-CT device, a PET-MRI device, etc. The scanner 110 may include a gantry 111, a detector 112, a detecting area 113, and a table 114. An object may be placed on the table 114. The table 114 may deliver the object to a target location in the scanning area 113. The detector 112 may detect radiation rays (e.g., gamma photons) emitted from the object in the scanning area 113. In some embodiments, the detector 112 may include a plurality of detection modules. The detection modules may be arranged in any structure, including but not limited to a ring (e.g., a detector ring), a rectangle, a triangle, or an array. Each of the plurality of detection module may include a scintillator array, a photoelectric converter, an energy information determination circuit and a time information determination circuit.

In practical application, a tracer (e.g., a radioactive isotope) may be injected into an object (e.g., blood vessels of a patient). The atoms of the tracer may be converted into biologically active molecules. The molecules may gather in tissues of the patient. When a sufficient amount of the molecules are estimated to be gathered in the tissues (usually in an hour), the patient may be positioned on the table 114. The radioactive isotope may undergo a positron emission decay (i.e., beta decay) and emits positrons. The positrons may interact with electrons inside the tissues (the interaction between positrons and electrons is called annihilation). The annihilations of the electrons and positrons may each produces a pair of annihilation photons (also referred to as gamma photons) that move in approximately opposite directions.

The gamma photons may be detected by the detector 112 and an image may be generated by the processing engine 140 based on information associated with the gamma photons. For example, the processing engine 140 may determine the time-of-flight (time information) associated with each of the pairs of gamma photons. Furthermore, the processing engine may determine the location where annihilation happens based on the time-of-flight. After obtaining a plurality of locations of annihilations, the processing engine 140 may generate a projection image (also referred to as a sonogram) based on the locations of the annihilations. The processing engine 140 may reconstruct images based on the projection image and reconstruction techniques such as filtered back projection (FBP). The reconstructed images may indicate the tissues that contains large number of biologically active molecules of the tracer. In some embodiments, the number of molecules of the tracer in a region may be related to biological functions of the tissues in the region. For example, if fluorodeoxyglucose (FDG) is used as the tracer in a PET scan, the number of tracer molecules in a region may be proportional to the rate of metabolism of glucose in the region. As tumors generally consume a huge amount of glucose, the region with large number of molecules may be identified in a reconstructed image as tumors.

The network 120 may include any suitable network that can facilitate exchange of information and/or data for the imaging system 100. In some embodiments, one or more components of the imaging system 100 (e.g., the scanner 110, the terminal 130, the processing engine 140, the storage 150, etc.) may communicate information and/or data with one or more other components of the imaging system 100 via the network 120. For example, the processing engine 140 may obtain image data (e.g., time information, energy information) from the scanner 110 via the network 120. As another example, the processing engine 140 may obtain user instructions from the terminal 130 via the network 120. The network 120 may include a public network (e.g., the Internet), a private network (e.g., a local area network (LAN), a wide area network (WAN)), etc.), a wired network (e.g., an Ethernet network), a wireless network (e.g., an 802.11 network, a Wi-Fi network, etc.), a cellular network (e.g., a Long Term Evolution (LTE) network), a frame relay network, a virtual private network ("VPN"), a satellite network, a telephone network, routers, hubs, witches, server computers, and/or any combination thereof. Merely by way of example, the network 120 may include a cable network, a wireline network, a fiber-optic network, a telecommunications network, an intranet, a wireless local area network (WLAN), a metropolitan area network (MAN), a public telephone switched network (PSTN), a Bluetooth™ network, a ZigBee™ network, a near field communication (NFC) network, or the like, or any combination thereof.

The terminal(s) 130 may include a mobile device 130-1, a tablet computer 130-2, a laptop computer 130-3, or the like, or any combination thereof. In some embodiments, the mobile device 130-1 may include a smart home device, a wearable device, a mobile device, a virtual reality device, an augmented reality device, or the like, or any combination thereof. In some embodiments, the terminal(s) 130 may be part of the processing engine 140.

The processing engine 140 may process data and/or information obtained from the scanner 110, the terminal(s)

130, and/or the storage 150. For example, the processing engine 140 may process image data (including time information, energy information, etc.) and reconstruct an image based on the image data. In some embodiments, the processing engine 140 may be a single server or a server group. The server group may be centralized or distributed. In some embodiments, the processing engine 140 may be local or remote. For example, the processing engine 140 may access information and/or data stored in the scanner 110, the terminal(s) 130, and/or the storage 150 via the network 120. As another example, the processing engine 140 may be directly connected to the scanner 110, the terminal(s) 130 and/or the storage 150 to access stored information and/or data. In some embodiments, the processing engine 140 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof. In some embodiments, the processing engine 140, or a portion of the processing engine 140 may be integrated into the scanner 110.

The storage 150 may store data, instructions, and/or any other information. In some embodiments, the storage 150 may store data obtained from the terminal(s) 130 and/or the processing engine 140. In some embodiments, the storage 150 may store data and/or instructions that the processing engine 140 may execute or use to perform exemplary methods described in the present disclosure. In some embodiments, the storage 150 may store image data (e.g., time information, energy information) obtained from the scanner 110. In some embodiments, the storage 150 may include a mass storage, a removable storage, a volatile read-and-write memory, a read-only memory (ROM), or the like, or any combination thereof.

In some embodiments, the storage 150 may be connected to the network 120 to communicate with one or more other components in the imaging system 100 (e.g., the processing engine 140, the terminal(s) 130, etc.). Alternatively or additionally, the storage 150 may be part of the processing engine 140.

Figure 2:
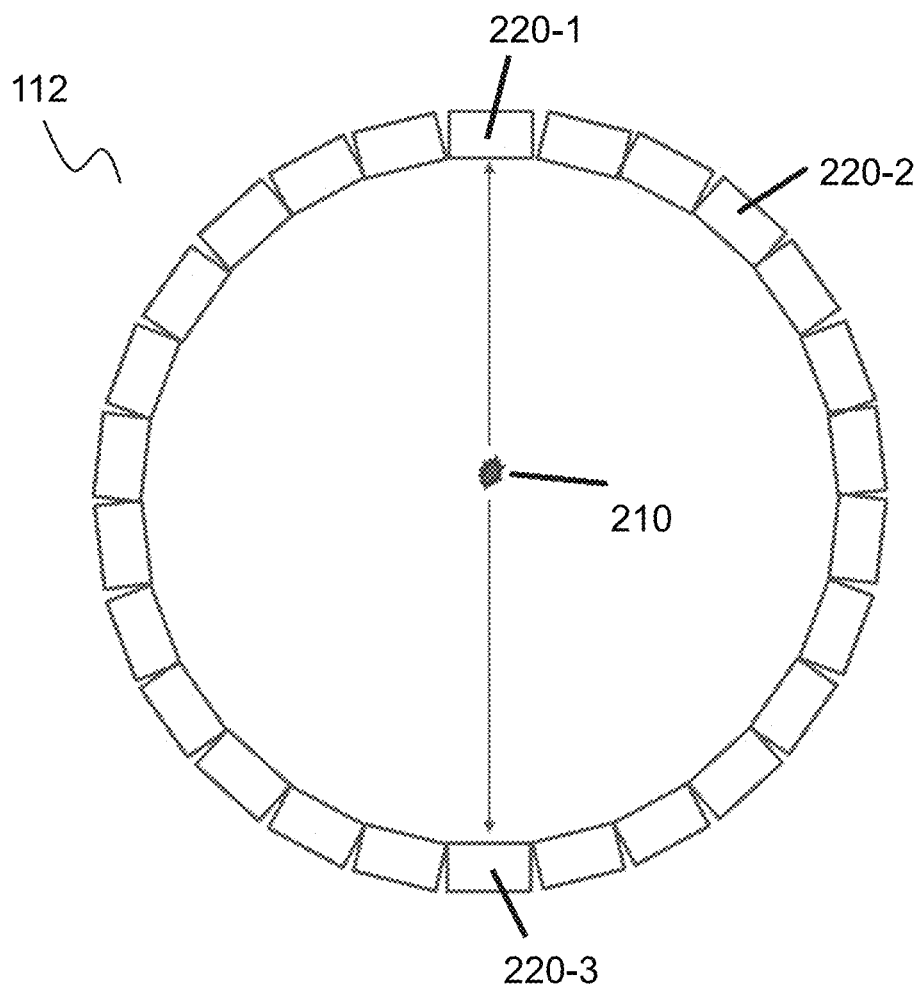
FIG. 2 is a schematic diagram illustrating an exemplary detector according to some embodiments of the present disclosure.

FIG. 2 is a schematic diagram illustrating an exemplary detector according to some embodiments of the present disclosure. As shown in FIG. 2, the detector 112 may include a plurality of detection modules 220 (e.g., 220-1, 220-2, 220-3, etc.). In some embodiments, an electron and a positron may be annihilated at a location 210, which produces a pair of annihilation photons that move in approximately opposite directions. The two annihilation photons may be detected by two detection modules (e.g., 220-1, 220-3), respectively. In some embodiments, the detection module 220 may include a scintillator array, one or more photoelectric converters, etc. The scintillator array may interact with a photon at an interaction point and generate one or more optical signals. The one or more photoelectric converters may be coupled to the scintillator array and convert the one or more optical signals to one or more electric signals. Detailed descriptions regarding the detection module 220 may be found in FIG. 3 and FIG. 7, and the descriptions thereof.

FIGS. 3A and 3B illustrate an exemplary detection module according to some embodiments of the present disclosure. FIG. 3A and FIG. 3B illustrate a top view and a perspective view of a detection module, respectively. As shown in FIGS. 3A and 3B, a detection module may include a scintillator array 310 and a plurality of photoelectric converters 320 (e.g., 320-1, 320-2, 320-3, 320-4, etc.). The scintillator array 310, as shown in FIGS. 3A and 3B (and also FIG. 3C), may include 4 rows of scintillation crystals (e.g., a scintillation crystal 340) and 5 columns of scintillation crystals. The plurality of photoelectric converters 320 may be coupled to the top surface of the scintillator array 310. In some embodiments, the plurality of photoelectric converters may be arranged in M rows and N columns. The space between adjacent photoelectric converters in a same row or column may be the same or different. For example, the M and the N is set to 2 in FIGS. 3A and 3B. In FIG. 3C, the M and N are 4 and 5, respectively. In some embodiments, each photoelectric converter may be coupled to more than one scintillation crystals, as shown in FIGS. 3A and 3B. Alternatively, as shown in FIG. 3C, more photoelectric converters are included and each photoelectric converter may be coupled to one scintillation crystal. In some embodiments, the M and the N each is an integer from 1 to 20. Detailed descriptions regarding the scintillator array 310 and the scintillation crystals may be found in FIG. 4 and the discerptions thereof.

In some embodiments, the scintillator array 310 may interact with a photon at an interaction point and generate a plurality of optical signals. The photoelectric converter 320 (or 330) may convert the plurality of optical signals to one or more electric signals. In some embodiments, each of the one or more electric signals may include an energy signal (also referred to as an anode signal) and a time signal (also referred to as a fast signal). Merely by way of example, the photoelectric converter may be a photomultiplier (PTM), an avalanche photodiode (APD), a silicon photomultiplier (SIPM), or the like.

Figure 4:
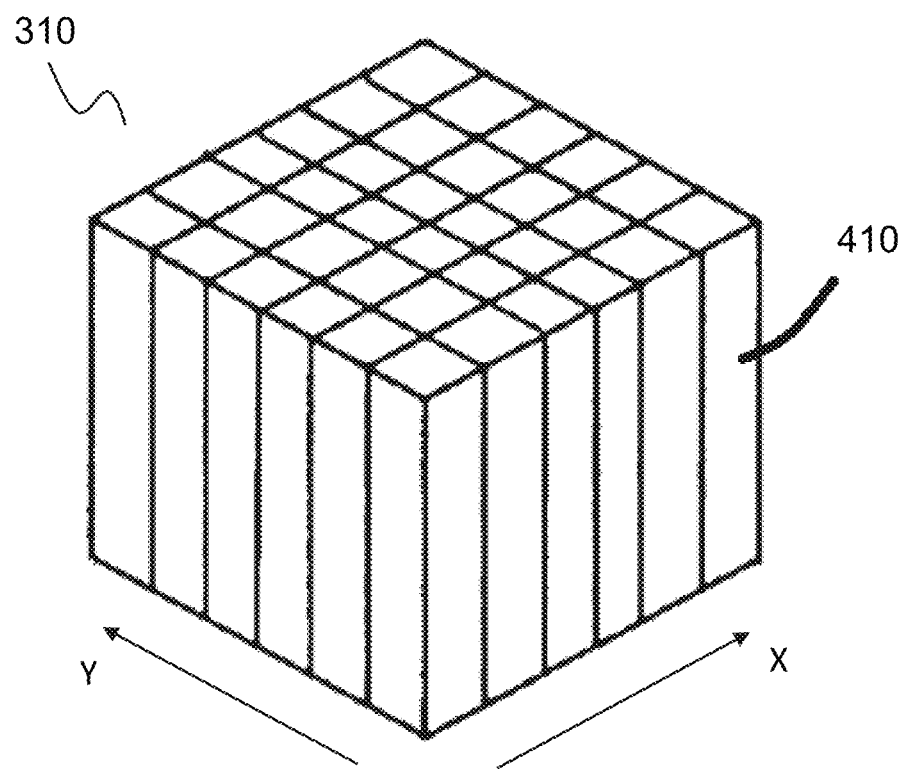
FIG. 4 is a schematic diagram illustrating an exemplary scintillator array according to some embodiments of the present disclosure.

FIG. 4 is a schematic diagram illustrating an exemplary scintillator array according to some embodiments of the present disclosure. As shown in FIG. 4, a scintillator array 310 may include a plurality of rows of scintillation crystals 410 arranged in a first direction (e.g., the direction of the X-axis) and a plurality of columns of scintillation crystals 410 arranged in a second direction (e.g., the direction of the Y-axis). The second direction may be approximately orthogonal to the first direction. In some embodiments, the row count of the plurality of rows of scintillation crystals 410 arranged in the X-axis direction (denoted as m) may equal the column count of the plurality of columns of scintillation crystals 410 arranged in the Y-axis direction (denoted as n). Merely by way of example, m is 6 and n is 6. As another examples, m and n may be 1, 2, 3, 4, 5, 6, 8, etc., respectively. In some embodiments, m may be the same as or different from n. For example, a scintillator array may have 3*4, 4*6, 6*5, 3*3, 5*5 scintillation crystals, or the like. In some embodiments, the scintillator array 310 may include only one scintillation crystal.

In some embodiments, the scintillation crystals in the scintillator array may be of the same size. In some embodiments, at least two scintillation crystals in the scintillator array may be of different sizes. In some embodiments, a scintillation crystal may have a shape of a cuboid, a cube, a cylinder, etc. At least one coating material including, e.g., an optical glue, a reflective material, etc., may be applied to at least part of a side of a scintillation crystal. The surface areas of scintillation crystals that are coated by a coating material may be different. In some embodiments, the scintillator array may include a flat surface (e.g., a top surface of the scintillation crystals). One or more photoelectric converters may be coupled to the flat surface of the scintillator array. In some embodiments, a scintillation crystal may include at least one material including, e.g., bismuth germanium oxide (BGO), lutetium-yttrium oxyorthosilicate (LYSO), lutetium oxyorthosilicate (LSO), etc.

Figure 5:
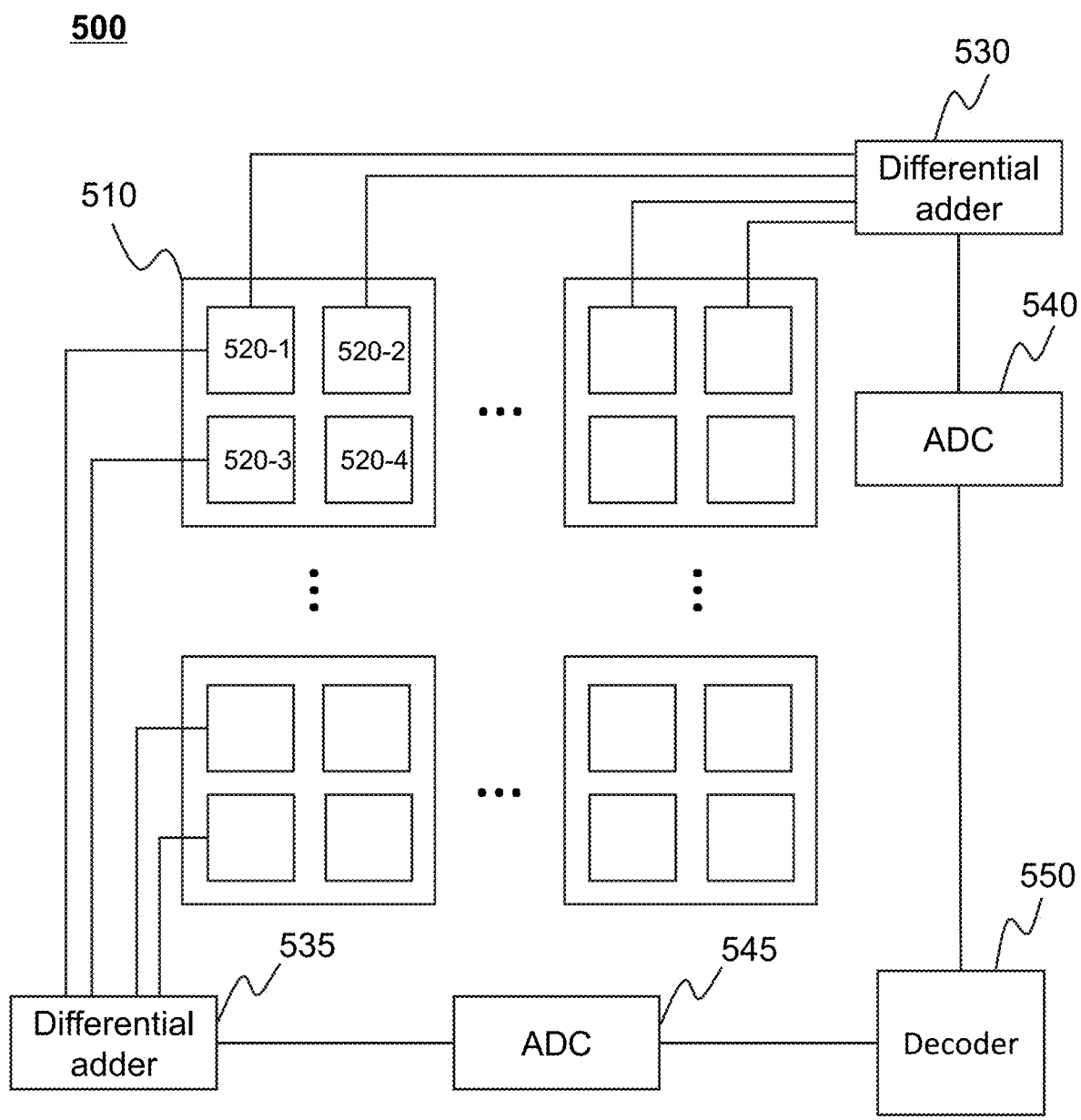
FIG. 5 is a schematic diagram illustrating an exemplary energy information determination circuit according to some embodiments of the present disclosure.

FIG. 5 is a schematic diagram illustrating an exemplary energy information determination circuit according to some embodiments of the present disclosure. As shown in FIG. 5, a detection module 500 may include a plurality of scintillator arrays (e.g., a scintillator array 510). One or more photoelectric converters may be coupled to each of the plurality of scintillator arrays. The photoelectric converters may be connected to an energy information determination circuit. The energy information determination circuit may be configured to provide energy information based on one or more energy signals. The energy information may illustrate a distribution of where the scintillation crystals and gamma photons interact and the intensity thereof. In some embodiments, the energy information determination circuit may include one or more row information determination circuits and one or more column information determination circuits. The row information determination circuits may each determine energy information of a row of photoelectric converters.

As shown in FIG. 5, a number of photoelectric converters 520 (e.g., 520-1, 520-2, 520-3 and 520-4) are coupled to the scintillator array 510. A row of photoelectric converters (e.g., the first row including 520-1 and 520-2) may be connected to a row information determination circuit. The row information determination circuit may include a differential adder 530 and an ADC 540. A row information determination circuit connected to a row of photoelectric converters may be connected to the decoder 550. A column of photoelectric converters (e.g., the first column including 520-1 and 520-3) may be connected to a column information determination circuit. The column information determination circuit may include a differential adder 535 and an ADC 545. A column information determination circuit connected to a column of photoelectric converters may also be connected to the decoder 550. A differential adder (e.g., the differential adder 530, the differential adder 535) may sum up electric signals from each of the photoelectric converters in the corresponding row/column. The ADC may convert an analog signal to a digital signal. The decoder 550 may decode the digital signal and generate the energy information. The decoder 550 may determine a location of an interaction point that a scintillator array interacts with a photon based on the energy information. In particular, as the gamma photon interacts with only some of the scintillation crystals, the energy signals generated by the photoelectric converters may have different intensities. For example, the intensity of an energy signal corresponding to a scintillation crystal that interacts with a gamma photon may be relatively higher than that corresponding to a scintillation crystal that does not interact with a gamma photon. The energy information may illustrate a distribution of where the scintillation crystals and the gamma photon interact and the intensity thereof. The intensity may relate to the number of interactions that occur at a location. Based on the generated energy information, the scintillation crystal with the highest intensity may be identified and its corresponding location may be determined as the location where the scintillation crystals and the gamma photon interact.

Figure 6:
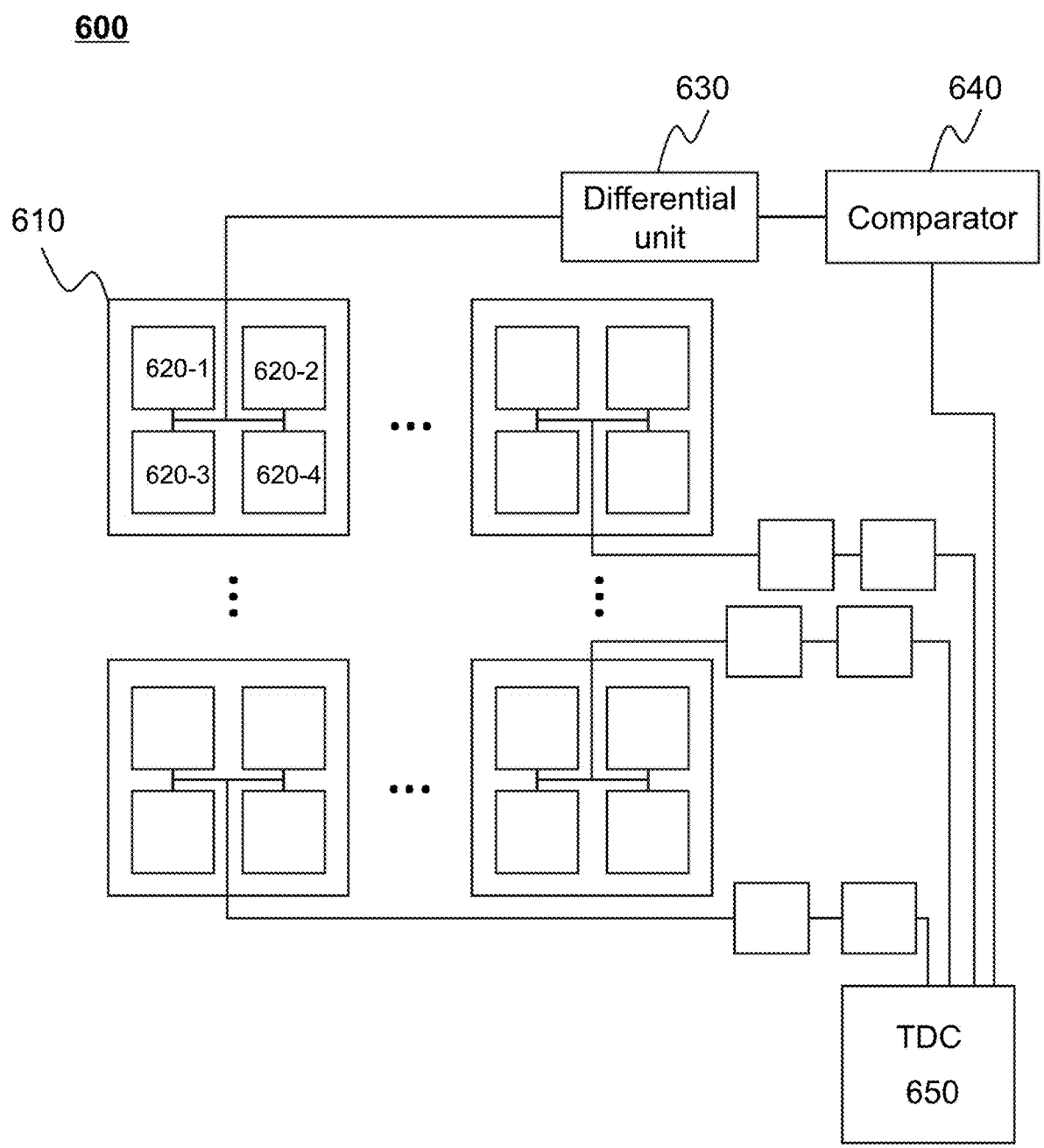
FIG. 6 is a schematic diagram illustrating an exemplary time information determination circuit according to some embodiments of the present disclosure.

FIG. 6 is a schematic diagram illustrating an exemplary time information determination circuit according to some embodiments of the present disclosure. The time information determination circuit may be configured to generate time information based on one or more time signals. The time information determination circuit may be connected to one or more photoelectric converters. As shown in FIG. 6, photoelectric converters (e.g., 620-1, 620-2, 620-3, 620-4) that are coupled to a same scintillator array (e.g., 610) may be connected to a time information determination circuit. The time information determination circuit may include a differential unit 630 and a comparator 640. In some embodiments, the differential unit 630 may process one or more time signals. Exemplary processing of the time signal may include summation, accelerating, smoothing, denoising, etc. For example, the time signal (or a summation of the one or more time signals) may be a cyclic signal that includes a high level section and a low level section in each cycle. A transitional section that the signal changes from the low level section to the high level section may be referred to as a rising edge. The differential unit 630 may accelerate the time signal by reducing the duration of the rising edge (e.g., making the rising edge steeper). The accelerated time signal may reach the high level section earlier, and the system may response faster to the accelerated time signal. In some embodiments, the differential unit 630 may be a high-pass differential circuit, such as a high-pass filter. The comparator 640 may generate a trigger signal based on the processed time signal. The time information determination circuit may include a time-to-digital converter (TDC) 650. The TDC 650 may generate time information based on the trigger signal from the comparators 640. In some embodiment, the time information may include a time point or a time slot when a scintillator array interacts with a photon. The TDC 650 may obtain a difference in the time of interaction between each of the scintillator arrays and the photons based on the time information. Furthermore, the TDC 650 may match the scintillator arrays where the received gamma photons are generated from a same annihilation event. Alternatively or additionally, the TDC 650 may calculate the location and time that the annihilation happens based on time information of the matched scintillator arrays.

Figure 7:
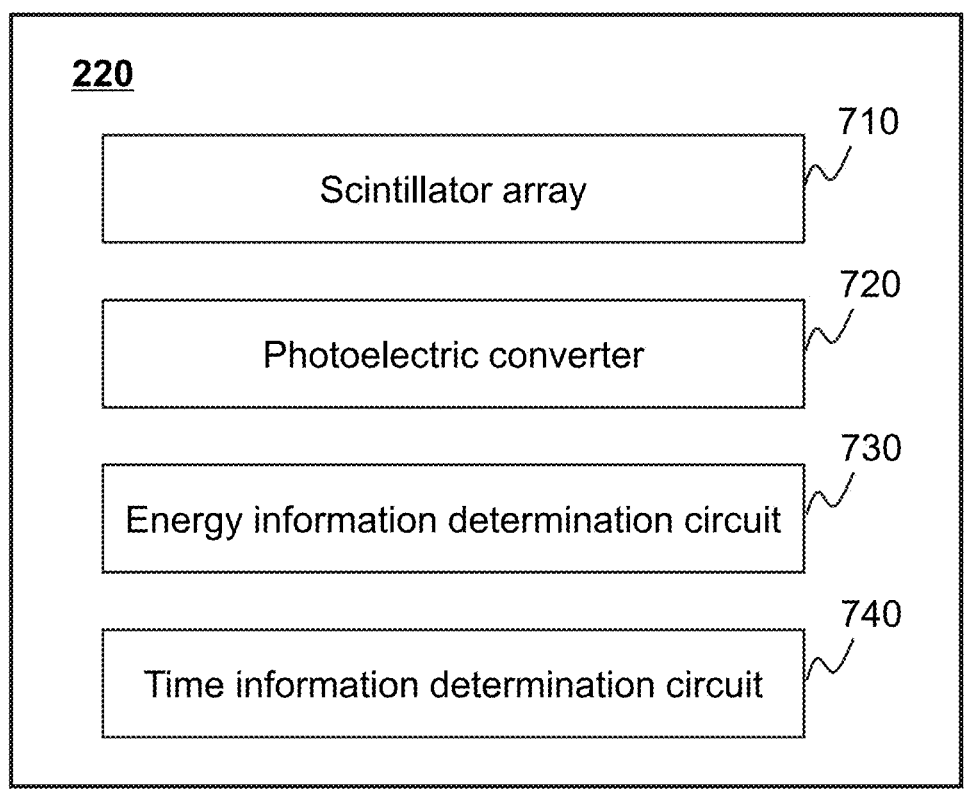
FIG. 7 is a block diagram illustrating an exemplary detection module according to some embodiments of the present disclosure.

FIG. 7 is a block diagram illustrating an exemplary detection module according to some embodiments of the present disclosure. As shown in FIG. 7, a detection module 220 may include a scintillator array 710, a photoelectric converter 720, an energy information determination circuit 730, and a time information determination circuit 740. The scintillator array 710 may interact with a photon at an interaction point to generate a plurality of optical signals. The detection module 220 may include more than one scintillator arrays 710. (e.g., 4 scintillator arrays). The scintillator array 710 may include one or more scintillation crystals.

In some embodiments, one or more photoelectric converters 720 may be coupled to a scintillator array 710. Each of the one or more photoelectric converters 720 may be coupled to one or more scintillation crystals of the scintillator array 710. The photoelectric converter 720 may convert the plurality of optical signals to one or more electric signals. An electric signal may include an energy component (or referred to as an energy signal) and a time component (or referred to as a time signal).

In some embodiments, at least one energy information determination circuit 730 may generate energy information based on the one or more energy signals. An energy information determination circuit 730 may be connected to one or more photoelectric converters 720. A time information determination circuit 740 may be connected to the one or more photoelectric converters 720. The time information determination circuit 740 may generate time information based on the one or more time signals. In some embodiments, the energy information determination circuit 730 and the time information determination circuit 740 may share one or more components. In some embodiments, the detection module 220 may include a switch circuit. The switch circuit may be used to control the work of the energy information determination circuit 730 and the time information determination circuit 740. For example, the energy information determination circuit 730 and the time information determination circuit 740 may work simultaneously or alternately.

Figure 8:
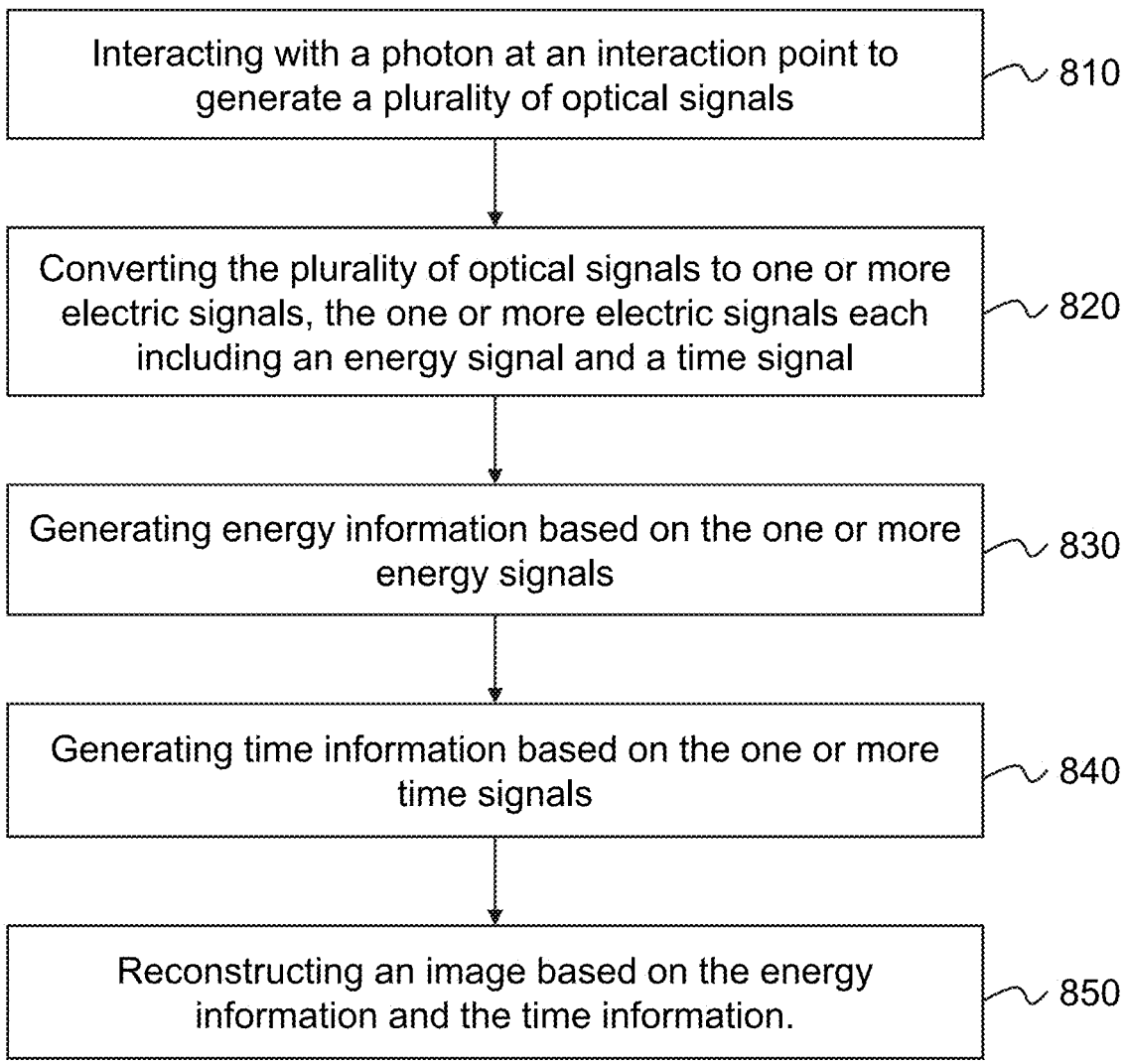
FIG. 8 is a flowchart illustrating an exemplary process for generating an image based on energy information and time information according to some embodiments of the present disclosure.

FIG. 8 is a flowchart illustrating an exemplary process 800 for generating an image based on energy information and time information according to some embodiments of the present disclosure. In some embodiments, one or more operations of process 800 illustrated in FIG. 8 for generating an image may be implemented in the system 100 illustrated in FIG. 1. For example, the process 800 illustrated in FIG. 8 may be stored in the storage 150 in the form of instructions, and invoked and/or executed by the processing engine 140. In particular, one or more operations of the process 800 may be implemented by the detection module 220 and/or the processing engine 140.

In 810, a scintillator array 710 may interact with a photon at an interaction point and generate a plurality of optical signals. The photon may be emitted from an annihilation event of an object. In some embodiments, a plurality of photons may be emitted. Each of the plurality of photons may strike on, and interacted with, a scintillator array 710. A plurality of scintillator arrays may be implemented in a detection module.

In 820, one or more photoelectric converters 720 may convert the plurality of optical signals to one or more electric signals. Each of the one or more electric signals may include an energy component (or referred to as an energy signal) and a time component (or referred to as a time signal). The one or more photoelectric converters 720 may be coupled to a scintillator array 710.

In 830, energy information determination circuit 730 may generate energy information based on the one or more energy signals. The at least one energy information determination circuit 730 each may be connected to some of the one or more photoelectric converters. In some embodiments, the energy information determination circuit 730 may include a row information determination circuit and a column information determination circuit. The row information determination circuit may be connected to a row of photoelectric converters. The column information determination circuit may be connected to a column of photoelectric converters.

In 840, time information determination circuit 740 may generate time information based on the one or more time signals. The time information determination circuit 740 may be connected to the one or more photoelectric converters 720 coupled to a scintillator array 710.

In 850, processing engine 140 may reconstruct an image based on the energy information and the time information. In some embodiments, the processing engine 140 may reconstruct the image based on reconstruction techniques such as filtered back projection (FBP). A reconstructed image may illustrate the tissues that contains a large number of biologically active molecules of the tracer.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure, and are within the spirit and scope of the exemplary embodiments of this disclosure.

Moreover, certain terminology has been used to describe embodiments of the present disclosure. For example, the terms "one embodiment," "an embodiment," and/or "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code, etc.) or combining software and hardware implementation that may all generally be referred to herein as a "unit," "module," or "system." Furthermore, aspects of the present disclosure may take the form of a computer program product embodied in one or more computer readable media having computer readable program code embodied thereon.

A computer readable signal medium may include a propagated data signal with computer readable program code embodied therein, for example, in baseband or as part of a carrier wave. Such a propagated signal may take any of a variety of forms, including electro-magnetic, optical, or the like, or any suitable combination thereof. A computer readable signal medium may be any computer readable medium that is not a computer readable storage medium and that may communicate, propagate, or transport a program for use by or in connection with an instruction execution system, apparatus, or device. Program code embodied on a computer readable signal medium may be transmitted using any appropriate medium, including wireless, wireline, optical fiber cable, RF, or the like, or any suitable combination of the foregoing.

Computer program code for carrying out operations for aspects of the present disclosure may be written in any combination of one or more programming languages, including an object oriented programming language such as JAVA, SCALA, SMALLTALK, EIFFEL, JADE, EMERALD, C++, C#, VB. NET, PYTHON or the like, conventional procedural programming languages, such as the "C" programming language, Visual Basic, Fortran 2013, PERL, COBOL 2012, PHP, ABAP, dynamic programming languages such as PYTHON, RUBY, and GROOVY, or other programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Furthermore, the recited order of processing elements or sequences, or the use of numbers, letters, or other designations therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose, and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software only solution, for example, an installation on an existing server or mobile device.

Similarly, it should be appreciated that in the foregoing description of embodiments of the present disclosure, various features are sometimes grouped together in a single embodiment, figure, or description thereof for the purpose of streamlining the disclosure aiding in the understanding of one or more of the various inventive embodiments. This method of disclosure, however, is not to be interpreted as reflecting an intention that the claimed subject matter requires more features than are expressly recited in each claim. Rather, inventive embodiments lie in less than all features of a single foregoing disclosed embodiment.

In some embodiments, the numbers expressing quantities or properties used to describe and claim certain embodiments of the application are to be understood as being modified in some instances by the term "about," "approximately," or "substantially." For example, "about," "approximately," or "substantially" may indicate ±20% variation of the value it describes, unless otherwise stated. Accordingly, in some embodiments, the numerical parameters set forth in the written description and attached claims are approximations that may vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the application are approximations, the numerical values set forth in the specific examples are reported as precisely as practicable.

Each of the patents, patent applications, publications of patent applications, and other material, such as articles, books, specifications, publications, documents, things, and/or the like, referenced herein is hereby incorporated herein by this reference in its entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that may be employed may be within the scope of the application. Thus, by way of example, but not of limitation, alternative configurations of the embodiments of the application may be utilized in accordance with the teachings herein. Accordingly, embodiments of the present application are not limited to that precisely as shown and described.

We claim:

1. A device, comprising:
 a plurality of detection modules, wherein each of the plurality of detection modules includes:
  a scintillator array, the scintillator array interacting with a plurality of photons at respective interaction points to generate a plurality of optical signals;
  one or more photoelectric converters coupled to the scintillator array and configured to convert the plurality of optical signals to one or more electric signals, the one or more electric signals each including an energy signal and a time signal, wherein the one or more photoelectric converters are arranged in M rows and N columns;
  M first energy information determination circuits, wherein each of the M first energy information determination circuits is connected to one of the M rows of photoelectric converters and configured to generate first energy information by summing up first energy signals that are generated by the one of the M rows of photoelectric converters;
  N second energy information determination circuits, wherein each of the N second energy information determination circuits is connected to one of the N columns of photoelectric converters and configured to generate second energy information by summing up second energy signals that are generated by the one of the N columns of photoelectric converters;
  a time information determination circuit connected to the one or more photoelectric converters and configured to generate time information of the interaction between the scintillator array and the plurality of photons based on the one or more time signals; and
 a processing engine, configured to generate an image based on the first energy information, the second energy information and the time information,
 wherein the time information determination circuit includes a differential unit connected to the one or more photoelectric converters, the differential unit being configured to:
  sum up the one or more time signals to generate a summation signal, wherein the summation signal is a cyclic signal and includes, in each cycle, a low level section, a high level section, and a transitional section that the summation signal changes from the low level section to the high level section; and
  reduce a duration of the transitional section of the summation signal to generate an accelerated time signal.

2. The device of claim 1, wherein the scintillator array includes a plurality of scintillation crystals; and
 each of the one or more photoelectric converters is coupled to one or more of the plurality of scintillation crystals.

3. The device of claim 1, wherein the M and the N each is an integer from 1 to 20.

4. The device of claim 1, wherein each of the M first energy information determination circuits and the N second energy information determination circuits includes a differential adder and an analog to digital converter (ADC).

5. The device of claim 1, further comprising a decoder connected to the M first energy information determination circuits and the N second energy information determination circuits, the decoder being configured to determine locations of the interaction points based on the first energy information and the second energy information.

6. The device of claim 1, wherein the time information determination circuit further includes:
   a comparator configured to generate a trigger signal based on the accelerated time signal; and
   a time-to-digital converter (TDC) configured to generate the time information based on the trigger signal.

7. The device of claim 1, wherein the time information includes a time point when the scintillator array interacts with the plurality of photons.

8. The device of claim 1, wherein the scintillator array is made of bismuth germanium oxide (BGO) crystals, lutetium-yttrium oxyorthosilicate (LYSO) crystals, or lutetium oxyorthosilicate (LSO) crystals.

9. The device of claim 1, wherein the photoelectric converter is a photomultiplier (PTM), an avalanche photodiode (APD), or a silicon photomultiplier (SIPM).

10. The device of claim 1, wherein the each of the plurality of detection modules further includes:
    a switch circuit, configured to control the M first energy information determination circuits, the N second energy information determination circuits and the time information determination circuit to work simultaneously or alternately.

11. A system, comprising:
    a gantry including a detecting area in which an object is scanned;
    a detector configured to receive a plurality of photons that are emitted from the object, the detector comprising:
        a plurality of detection modules, wherein each of the plurality of detection modules includes:
        a scintillator array, the scintillator array interacting with a plurality of photons at respective interaction points to generate a plurality of optical signals;
        one or more photoelectric converters coupled to the scintillator array and configured to convert the plurality of optical signals to one or more electric signals, the one or more electric signals each including an energy signal and a time signal, wherein the one or more photoelectric converters are arranged in M rows and N columns;
        M first energy information determination circuits, wherein each of the M first energy information determination circuits is connected to one of the M rows of photoelectric converters and configured to generate first energy information by summing up first energy signals that are generated by the one of the M rows of photoelectric converters;
        N second energy information determination circuits, wherein each of the N second energy information determination circuits is connected to one of the N columns of photoelectric converters and configured to generate second energy information by summing up second energy signals that are generated by the one of the N columns of photoelectric converters; and
        a time information determination circuit connected to the one or more photoelectric converters and configured to generate time information of the interaction between the scintillator array and the plurality of photons based on the one or more time signals; and
    a processing engine, configured to generate an image based on the first energy information, the second energy information and the time information,
    wherein the time information determination circuit includes a differential unit connected to the one or more photoelectric converters, the differential unit being configured to:
        sum up the one or more time signals to generate a summation signal, wherein the summation signal is a cyclic signal and includes, in each cycle, a low level section, a high level section, and a transitional section that the summation signal changes from the low level section to the high level section; and
        reduce a duration of the transitional section of the summation signal to generate an accelerated time signal.

12. The system of claim 11, wherein the scintillator array includes a plurality of scintillation crystals; and
    each of the one or more photoelectric converters is coupled to one or more of the plurality of scintillation crystals.

13. The system of claim 11, wherein each of the M first energy information determination circuits and the N second energy information determination circuits includes a differential adder and an analog to digital converter (ADC).

14. The system of claim 11, wherein each of the plurality of the detection modules further includes: a decoder connected to the M first energy information determination circuits and the N second energy information determination circuits, the decoder being configured to determine locations of the interaction points based on the first energy information and the second energy information.

15. The system of claim 11, wherein the each of the plurality of detection modules further includes:
    a switch circuit, configured to control the M first energy information determination circuits, the N second energy information determination circuits and the time information determination circuit to work simultaneously or alternately.

16. A method, comprising:
    interacting, by a scintillator array, with a plurality of photons at respective interaction points to generate a plurality of optical signals;
    converting, by one or more photoelectric converters coupled to the scintillator array, the plurality of optical signals to one or more electric signals, the one or more electric signals each including an energy signal and a time signal, wherein the one or more photoelectric converters are arranged in M rows and N columns;
    generating, by each of M first energy information determination circuits connected to one of the M rows of photoelectric converters, first energy information by summing up first energy signals that are generated by the one of the M rows of photoelectric converters;
    generating, by each of N second energy information determination circuits connected to one of the N columns of photoelectric converters, second energy information by summing up second energy signals that are generated by the one of the N columns of photoelectric converters;
    generating, by a time information determination circuit connected to the one or more photoelectric converters, time information of the interaction between the scintillator array and the plurality of photons based on the one or more time signals; and
    generating, by a processing engine, an image based on the first energy information, the second energy information and the time information, wherein the generating time information of the interaction between the scintillator array and the plurality of photons based on the one or more time signals includes:
  summing up, by a differential unit of the time information determination unit, the one or more time signals to generate a summation signal, wherein the summation signal is a cyclic signal and includes, in each cycle, a low level section, a high level section, and a transitional section that the summation signal changes from the low level section to the high level section;
  reducing, by the differential unit, a duration of the transitional section of the summation signal to generate an accelerated time signal.

17. The method of claim 16, further comprising:
determining, by a decoder connected to the M first energy information determination circuits and the N second energy information determination circuits, locations of the interaction points based on the first energy information and the second energy information.

18. The method of claim 16, further comprising:
generating, by a comparator, a trigger signal based on the accelerated time signal; and
generate, by a time-to-digital converter (TDC), the time information based on the trigger signal.

19. The method of claim 16, wherein the time information includes a time point when the scintillator array interacts with the plurality of photons.

\* \* \* \* \*